US012016592B2

(12) United States Patent
Riccione (10) Patent No.: US 12,016,592 B2
(45) Date of Patent: Jun. 25, 2024

(54) EXTERNAL BONE FIXATION SYSTEM

(71) Applicant: Trilliant Surgical, LLC, Houston, TX (US)

(72) Inventor: Nicholas Riccione, Boca Raton, FL (US)

(73) Assignee: Trilliant Surgical, LLC, Houston, TX (US)

( * ) Notice: Subject to any disclaimer, the term of this patent is extended or adjusted under 35 U.S.C. 154(b) by 33 days.

(21) Appl. No.: 17/681,379

(22) Filed: Feb. 25, 2022

(65) Prior Publication Data

US 2022/0249129 A1 Aug. 11, 2022

Related U.S. Application Data

(63) Continuation of application No. 16/379,547, filed on Apr. 9, 2019, now Pat. No. 11,291,476, which is a continuation of application No. 15/178,977, filed on Jun. 10, 2016, now Pat. No. 10,258,378.

(51) Int. Cl.
*A61B 17/62* (2006.01)
*A61B 17/00* (2006.01)
*A61B 17/64* (2006.01)

(52) U.S. Cl.
CPC .......... *A61B 17/62* (2013.01); *A61B 17/6416* (2013.01); *A61B 17/6425* (2013.01); *A61B 17/6433* (2013.01); *A61B 17/6466* (2013.01); *A61B 2017/00853* (2013.01); *A61B 2017/00858* (2013.01)

(58) Field of Classification Search
CPC .................................................... A61B 17/62
See application file for complete search history.

(56) References Cited

U.S. PATENT DOCUMENTS

| | | | |
|---|---|---|---|
| D32,509 S | 4/1900 | Gilson |
| D82,369 S | 10/1930 | Cafieho |
| D239,364 S | 3/1976 | Mooney |
| 4,483,334 A | 11/1984 | Murray |
| 4,486,664 A | 12/1984 | Wollnik |

(Continued)

FOREIGN PATENT DOCUMENTS

FR 133244-0002 8/1984

OTHER PUBLICATIONS

CLAW II Surgical Technique pp. 1-3, http://www.wmt.com/footandankle/FA042-112.asp Aug. 15, 2013.

(Continued)

*Primary Examiner* — Tessa M Matthews
(74) *Attorney, Agent, or Firm* — Veros Legal Solutions, LLP (57) ABSTRACT

An external bone fixation system may include a first semi-circular external fixation member, a second semi-circular external fixation member, four ball collet assemblies attached to the second external fixation member, and four shafts. Each shaft may include a first end attached to the first external fixation member and a second end with a stop member, and each of the four shafts extends slidably through an opening in a ball of one of the four ball collet assemblies. The stop member of each second end prevents each second end from passing through the opening in its respective ball. Each shaft also includes a hinge located closer to the first end than to the second end.

8 Claims, 10 Drawing Sheets

(56) References Cited

U.S. PATENT DOCUMENTS

| | | |
|---|---|---|
| 4,620,533 A | 11/1986 | Mears |
| 4,628,922 A | 12/1986 | Dewar |
| D296,777 S | 7/1988 | Cornell |
| D296,984 S | 8/1988 | Mashburn |
| D298,510 S | 11/1988 | Marsh |
| 5,060,753 A | 10/1991 | Hopkins et al. |
| 5,443,464 A | 12/1995 | Russell et al. |
| 5,683,389 A | 11/1997 | Orsak |
| 5,746,741 A | 5/1998 | Kraus et al. |
| 5,921,985 A | 7/1999 | Ross |
| 5,947,999 A | 9/1999 | Groiso |
| 6,082,491 A | 7/2000 | Collier et al. |
| 6,162,223 A | 12/2000 | Orsak |
| 6,277,119 B1 | 8/2001 | Walulik |
| 6,340,361 B1 | 1/2002 | Kraus et al. |
| 6,409,729 B1 | 6/2002 | Martinelli |
| 6,482,206 B2 | 11/2002 | Schoenefeld |
| 6,730,086 B2 | 5/2004 | Hehli |
| D507,481 S | 7/2005 | Blake |
| D509,726 S | 9/2005 | Diller |
| D536,607 S | 2/2007 | Bekkevold |
| D537,334 S | 2/2007 | Lee |
| D562,677 S | 2/2008 | Farber et al. |
| D564,871 S | 3/2008 | Pitcher |
| D574,702 S | 8/2008 | Stephens |
| 7,465,303 B2 | 12/2008 | Riccione et al. |
| 7,678,112 B2 | 3/2010 | Rezach |
| 8,235,994 B2 | 8/2012 | Hollawell |
| 8,585,703 B2 | 11/2013 | Verma |
| 9,084,630 B2 | 7/2015 | Mullaney |
| D758,177 S | 6/2016 | Riccione |
| 9,370,380 B2 | 6/2016 | Riccione |
| 10,022,152 B2 | 7/2018 | Riccione |
| 10,258,378 B2 | 4/2019 | Riccione |
| 10,687,853 B2 | 6/2020 | Riccione |
| 2003/0187432 A1 | 10/2003 | Johnson et al. |
| 2005/0080319 A1 | 4/2005 | Dinkler, II et al. |
| 2006/0081553 A1 | 4/2006 | Patterson |
| 2006/0184169 A1* | 8/2006 | Stevens ................. A61B 17/62 606/54 |
| 2007/0233061 A1 | 10/2007 | Lehmann et al. |
| 2007/0284188 A1 | 12/2007 | Chippendale |
| 2008/0167666 A1 | 7/2008 | Fiere |
| 2008/0167688 A1 | 7/2008 | Fauth |
| 2008/0223656 A1 | 9/2008 | John |
| 2008/0275507 A1 | 11/2008 | Triplett et al. |
| 2008/0319443 A1 | 12/2008 | Focht |
| 2009/0088751 A1 | 4/2009 | Mullaney |
| 2009/0198235 A1 | 8/2009 | Steiner |
| 2010/0023062 A1 | 1/2010 | Faillace |
| 2010/0131065 A1 | 5/2010 | Burke |
| 2010/0312243 A1 | 12/2010 | Ross et al. |
| 2011/0251614 A1 | 10/2011 | Piraino |
| 2012/0209266 A1 | 8/2012 | Ottoboni et al. |
| 2014/0025076 A1 | 1/2014 | Lee et al. |
| 2014/0276815 A1* | 9/2014 | Riccione ............ A61B 17/6416 606/54 |
| 2014/0276816 A1 | 9/2014 | Cresina et al. |
| 2014/0309639 A1 | 10/2014 | Averous |
| 2014/0371801 A1 | 12/2014 | Dall et al. |
| 2015/0230839 A1 | 8/2015 | Riccione |
| 2016/0278812 A1 | 9/2016 | Riccione |
| 2016/0278813 A1 | 9/2016 | Riccione |
| 2017/0042579 A1 | 2/2017 | Mannanal |
| 2017/0246483 A1 | 8/2017 | Riccione |
| 2018/0317966 A1 | 11/2018 | Riccione |
| 2018/0344354 A1* | 12/2018 | Mullaney ............. A61B 17/645 |
| 2019/0231393 A1 | 8/2019 | Riccione |
| 2020/0315661 A1 | 10/2020 | Riccione |
| 2022/0346983 A1* | 11/2022 | Arnette ................. A61F 2/60 |
| 2022/0354539 A1* | 11/2022 | Ferrante ............... A61B 17/62 |

OTHER PUBLICATIONS

Company Seven TeleVue NP101 Telescope (2011) Specification/Description Page, mounting hardware, website copyright 2011, online, http://www.company7.com/televue/telescopes/tvnp101.html, [site visited Sep. 28, 2015 2:12:05 AM], 13 pages.

Integra MID & Hindfoot Solutions Uni-CP Compression Plate pp. 1-3, http://ilstraining.com/MID%20%20Hindfoot%20Solutions/Uni_C . . . Aug. 15, 2013.

Specialty Arborist Pulleys: Self-Jamming Pulleys, Swivel Pulleys, and More, website copyright 2010, online, http://www.wesspur.com/pulleys/self-jamming-pulleys.html, [site visited Sep. 28, 2015 2:15:36 AM], 6 pages.

* cited by examiner

EXTERNAL BONE FIXATION SYSTEM

CROSS-REFERENCE TO RELATED APPLICATION

This application is a Continuation of U.S. patent application Ser. No. 15/178,977, filed Jun. 10, 2016, and entitled "External Bone Fixation System," the entirety of which is hereby incorporated by reference.

FIELD

The present application is related to medical devices, systems and methods. More specifically, the present application describes an external bone fixation device, system and method.

BACKGROUND

External fixation devices have been commonly used for various treatments of bone conditions. Such bone conditions include leg lengthening, osteotomies, arthrodesis, open fracture fixations, compound fracture fixations, and other bone conditions amenable to treatment by use of an external fixation assembly. For example, external fixation devices are typically used in treatment of bones when frequent wound care is necessary to treat an open wound or a surgical site within an extremity.

Although current external fixation devices are often adequate, many external fixation devices are relatively large, include numerous components, are complicated to use, difficult to adjust, and involve challenging postoperative care and use. For example, current external fixation devices involve relatively large and numerous components, creating operative difficulties to the practitioner and postoperative difficulties to the patient. Many devices, for instance, involve a ring or "halo" member disposed about an affected area to provide support to pins for fixating bone matter. Such components, however effective, are relatively bulky and create difficulty for the physician to insert the pins and for the patient to move independently.

These ring or halo fixation devices are often used, for example, by orthopedic surgeons and podiatrists in the treatment of foot injuries and maladies. Some injuries or conditions involving the foot or ankle require that these devices be applied to the bones of the foot (e.g., calcaneus, tarsals, metatarsals, and phalanges) and the lower leg bones (e.g., tibia and fibula). In such circumstances, pins may be inserted into both the foot and lower leg bones, in order to secure the fixation device. Currently available external bone fixation systems, however, have limited rotational ability for a given pin, which is exacerbated by the complex and varied placement pins used for different patients with different anatomies and injuries.

Therefore, it would be advantageous to have improved external bone fixation devices, systems and methods. Ideally, an improved external bone fixation system would be relatively simpler than currently available systems, for example having fewer components and/or being less bulky and cumbersome for the physician and the patient. Also ideally, the improved system would allow for easier, simpler and more secure connections between the external fixation components and one or more bone pins connecting the system to the patient's bone(s), including improved rotational ability about the pin(s). At least some of these objectives will be addressed by the embodiments described in this application.

DESCRIPTION OF PRIOR ART

One example of a prior art approach is found in U.S. Pat. No. 7,465,303 (Riccione et al.). Among other embodiments, Riccione teaches the use of a plurality of compression nuts, the threads of which are mateable with the threads of a threaded rod. Riccione further describes one or more collets, comprising collet sleeves and collet nuts. The one or more collets are configured to hold a bone pin and form a compression lock in the apertures, when the collet nuts are tightened against the pin holding elements during use. This patent, however, fails to teach multiple orientational components, such as a slideable bracket, a collet and/or other components, which may be fixed in location through the use of a single fastener.

Another discussion of a prior art approach may be found in U.S. Pat. No. 8,235,994 (Hollawell), which teaches a fixator for use in the reconstruction of acute, chronic and traumatic injuries to the upper and lower extremities. Specifically, Hollawell describes a clamping system that allows for the snapping in of pins and rails, and for multi-planar fixation of bones. Hollawell fails to teach, however, the ability to independently rotate and set a pin within a collet clamp having a fixed location. Hollawell also does not describe the ability to have multiple independently rotatable axes for fixing a pin location, where the system may be fixed in location using a single fastener.

Definition of Terms

The terms "rod," "pin" and "nail" are used interchangeably. All three terms refer to a rigid, elongate component that is inserted into one or more bones for the purpose of anchoring, stabilizing, repairing, or supporting the bone(s). The term "rod" usually implies a relatively large device, while the term "pin" implies a somewhat smaller device; however, there is no clear boundary between these terms. In addition, the term "rod" (and the terms "rail" and "tube") is not limited to any particular cross-sectional shape, and may in fact be circular, oval, square, rectangular, polygonal or any combination thereof, while still falling within the term "rod" as used herein.

As used herein, the term "threaded" indicates that a rod or pin has screw-type threads on its external surface; however, a non-threaded rod or pin can have one or more threaded holes passing through it, for fixation screws, so long as the threads are not exposed on the external surface. A rod externally threaded along at least a part thereof is generally referred to as a screw. The screws maybe threaded at one or both ends, based on the preferred use of the screw. In some cases, however, non-threaded rods or pins can be used and would still fall within the scope of a "threaded engagement" as used herein, especially where the non-threaded pin is attached to another element (e.g., bone, plate, rod, pin) sufficiently to hold the rod to the element.

While the terms "rod," "pin" and "nail" normally tend to imply that an implant does not have an externally threaded surface, some implanted rods, pins and nails have external threads.

Where alternative meanings are possible, the broadest meaning is intended. All words used in this application are intended to be used in the normal, customary usage of grammar and the English language.

BRIEF SUMMARY

The embodiments described herein provided improved devices, systems and methods for external bone fixation. In one aspect, an external bone fixation assembly includes a fracture fusion tube, with a bracket slidably engaged thereon. The assembly further includes a collet clamp connected to the bracket, with a perforated ball rotatably seated within the clamp, the ball having an aperture for receiving a bone bin therethrough. The assembly uses a single screw for threadably engaging the pin collet, the clamp and the bracket, such that the position of the ball, bracket, and collet clamp is fixed. Thus, the assembly for external bone fixation has multiple axes of rotation for pin placement and setting, where the desired placement may be fixed through the use of a single screw or similar connector.

The apparatus and method of the present invention generally includes an external bone pin assembly that includes a fracture fusion tube for slidably engaging one or more bracket (which may be a clamp or similar structure). At least one bracket is connected to a collet clamp or similar structure which is rotatable around the circumference of the fracture fusion tube. The collet clamp has seated therein a perforated ball for receiving a bone pin therethrough, the ball being rotatable within the collet clamp for adjusting the angle of engagement for the bone pin and the bone. The perforated ball is composed of aluminum or a similar crushable material. The collet clamp and the bracket have aligned apertures, at least one of which is threaded, and a single screw can be aligned with both apertures, such that tightening a single screw will secure the bracket and collet clamp into a fixed position, and the compressive force of the collet clamp from the tightening screw on the perforated ball crimps the ball into a fixed position. Thus, a single screw can fix all of the components from a given pin subassembly extending from the fusion fracture tube. The embodiments herein thus provide an external bone pin assembly for a simpler assembly, which provides greater pin insertion into metatarsals and other bones in the foot, though alternative embodiments may be applied to other bodily regions, including the tibia and other bones, using a larger scale but similar principle of operation.

In another aspect, an external bone fixation system may include: a first semi-circular external fixation member; a second semi-circular external fixation member; four ball collet assemblies attached to the second external fixation member; and four shafts, each shaft having a first end attached to the first external fixation member and a second end comprising a stop member. Each of the four shafts extends slidably through an opening in a ball of one of the four ball collet assemblies. The stop member of each second end prevents each second end from passing through the opening in its respective ball, and each shaft also includes a hinge located closer to the first end than to the second end.

In some embodiments, the first external fixation member and the second external fixation member are horseshoe shaped. In some embodiments, the first external fixation member includes four lateral protrusions, each of which includes a shaft attachment aperture to which one of the first ends of the four shafts is attached. In some embodiments, the first external fixation member includes at least four shaft attachment apertures equally spaced around the first external fixation member, and each of the first ends of the shafts is attached to the first external fixation member via one of the shaft attachment apertures. In some embodiments, the first ends of the shafts are attached to the first external fixation member such that they can spin within, but cannot pass vertically through, the shaft attachment apertures. Some embodiments may include more than four attachment apertures, equally spaced along the first external member, such that any of the first ends of the shafts may be detached from a first attachment aperture and moved to a second attachment aperture. For example, in some embodiments there may be at least thirty attachment apertures. In some embodiments, the second external fixation member may include at least four collet attachment apertures, equally spaced around the second external fixation member, and each of the ball collet assemblies is attached to the second external fixation member via one of the collet attachment apertures. In some embodiments, the second external fixation member may be configured to slide along the four shafts from a collapsed configuration, in which the second external fixation member is located between the hinges of the shafts and the first external fixation member, to a fully extended configuration, in which the second external fixation member contacts the stop members of the four shafts.

Each ball collet assembly may include, in some embodiments: a ball with a central opening and multiple longitudinal slits; an insert with multiple longitudinal slits and configured to fit over the ball; and a clamp configured to fit over the insert and having only one adjustment member to tighten the clamp over the liner and the ball. In some embodiments, the ball may be made of aluminum with a rough surface coating, and the insert may be made of PEEK plastic. In one embodiment, the ball of each ball collet assembly may include: at least one full thickness, full length slit, extending from one end of the ball to an opposite end and from the central opening to an outer surface of the ball; and at least one partial slit, which includes a full thickness portion extending from the central opening to the outer surface, and a partial thickness portion extending only partway from the central opening to the outer surface. In some embodiments, the full thickness portion may include two lengths of the partial slit, located at opposite ends of the central opening, and the partial thickness portion may be located between the two lengths of the full thickness portion. The clamp may include a threaded aperture for accepting a screw to tighten the clamp, and a surface of the threaded aperture may be coated with Teflon.

In some embodiments, the external bone fixation system may also include at least one bone pin attachment member configured to attach to the first external fixation member or the second external fixation member and to a bone pin. The system may also optionally include a third semi-circular external fixation member, at least four additional ball collet assemblies, and at least two additional shafts. At least two of the additional ball collet assemblies are attached to the third external fixation member, and at least two of the additional ball collet assemblies are attached to the first external fixation member. The shafts are slidably coupled between the ball collet assemblies attached to the third external fixation member and the ball collet assemblies attached to the first external fixation member.

In another aspect, a ball collet assembly for use with an external bone fixation system may include: a ball with a central opening and multiple longitudinal slits; an insert configured to fit over the ball and having multiple longitudinal slits; and a clamp configured to fit over the insert and having only one adjustment member to tighten the clamp over the liner and the ball. Again, the ball may be made of aluminum with a rough surface coating, and the insert may be made of PEEK plastic, in some embodiments. The ball may include at least one full thickness, full length slit, extending from one end of the ball to an opposite end and from the central opening to an outer surface of the ball. The ball may also optionally include at least one partial slit, which may include a full thickness portion extending from the central opening to the outer surface and a partial thickness portion extending only partway from the central opening to the outer surface.

In yet another aspect, a method for attaching an external bone fixation system to one or more bones in a lower limb of a patient may involve: positioning a first semi-circular external fixation member over the lower limb at a first location; sliding a second semi-circular external fixation member along four shafts attached to the first external fixation member and extending through central openings of four ball collet assemblies attached to the second external fixation member, to position the second external fixation member over the lower limb at a second location; tightening the four ball collet assemblies attached to the second external fixation member to fix the ball collet assemblies immovably to the four shafts, thus locking positions of the first external fixation member, the second external fixation member and the four shafts, relative to one another; and attaching a first bone pin attachment member coupled with the first external fixation member with a first bone pin extending out of a first bone in the lower limb.

Optionally, the method may also include twisting the first external fixation member, relative to the second external fixation member, by bending the four shafts at four hinges in the shafts, where each of the four shafts includes one of the four hinges. The method may also optionally include straightening the four shafts via hinges located on the four shafts, before sliding the second external fixation member from a first position, in which it is located between the four hinges and the first external fixation member, to a second position, in which the hinges are located between the first and second external fixation members. In some embodiments, sliding the second external fixation member along the four shafts expands the external bone fixation from a collapsed configuration to an expanded configuration by straightening the four shafts at four hinges. In some embodiments, sliding the second external fixation member along the four shafts involves sliding the second external fixation member until it contacts four stop members attached to ends of the four shafts.

The method may also optionally involve attaching a second bone pin attachment member coupled with the first external fixation member with a second bone pin extending out of the first bone or a second bone in the lower limb. Optionally, the method may also involve attaching a second bone pin attachment member coupled with the second external fixation member with a second bone pin extending out of the first bone or a second bone in the lower limb. In some embodiments, tightening each of the four ball collet assemblies over each of the four shafts may involve tightening only one screw of each of the four ball collet assemblies.

These and other aspects and embodiments are described in greater detail below, in reference to the attached drawing figures.

DETAILED DESCRIPTION

Set forth below is a description of various embodiments of devices, systems and methods for external bone fixation. Future and present alternatives and modifications to these embodiments are contemplated within the scope of the present application. Any alternatives or modifications that make insubstantial changes in function, purpose, structure or result to the described embodiments are intended to be included within the scope of the invention as set forth in the claims.

Figure 1:
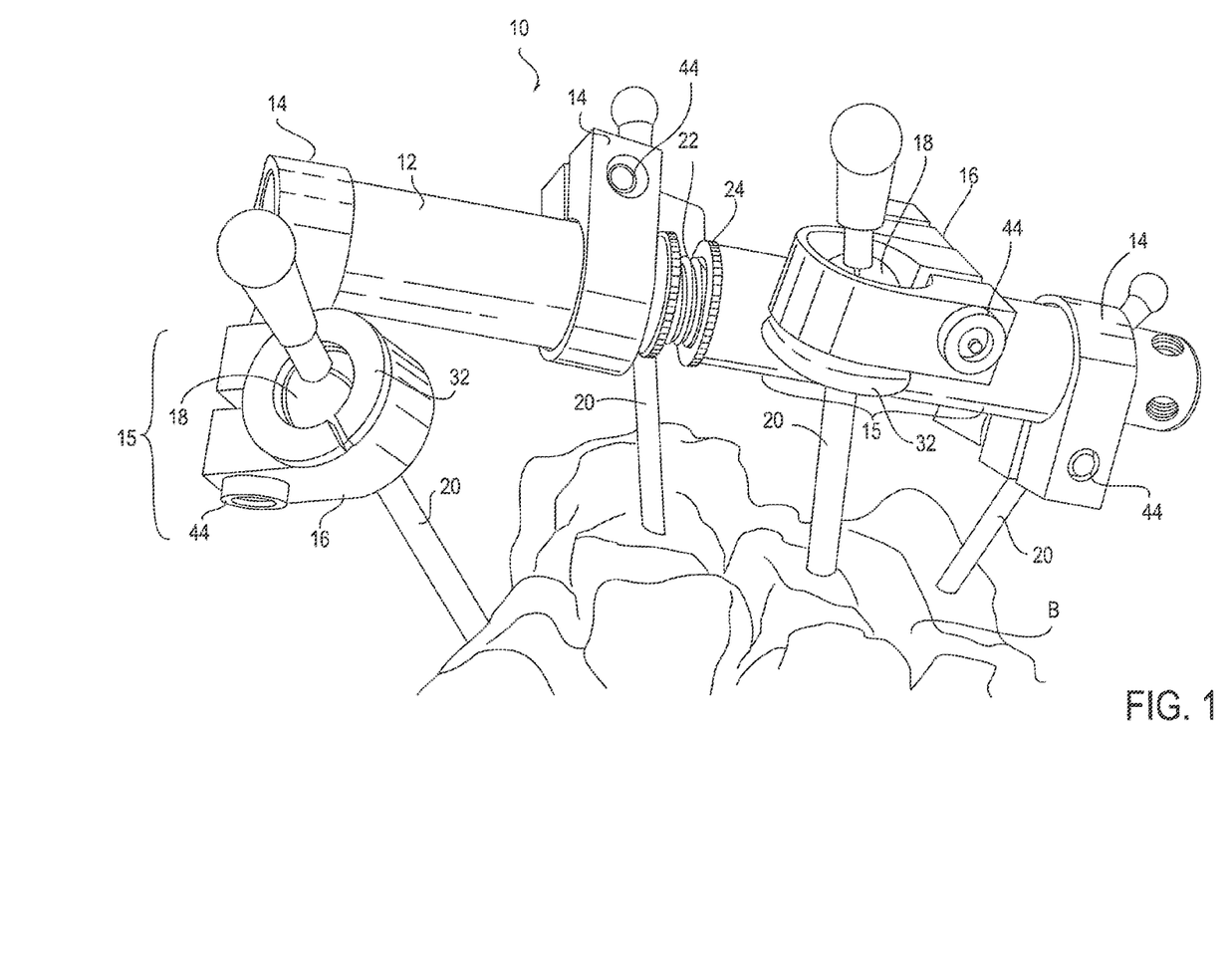
FIG. 1 is a perspective view of an external bone fixation rail system, applied to metatarsal bones, according to one embodiment.

Referring to FIG. 1, in one embodiment, an external bone fixation rail system 10 includes a bone fusion tube or rail 12, at least one bracket 14, and at least one ball collet assembly 15. Each ball collet assembly 15 includes a collet clamp 16, an insert 32 disposed within collet clamp 16, and a ball collet 18 (or simply "ball") disposed within insert 32. Rail system 10 may also include one or more bone pins 20 for attaching system 10 to bone(s) B. In various embodiments, however, bone pins 20 may be standard pins or rods used in a bone fixation procedure and might not be provided as part of system 10. Brackets 14 are attached to rail 12, collet clamps 16 are attached to brackets 14, and bone pins 20 are inserted through ball collets 18.

A fastener 44 extends through each coupled pair of bracket 14 and collet clamp 16. When fastener 44 is relatively loose, its corresponding bracket 14 is free to slide along, and rotate around, rail 12. When fastener 44 is relatively loose, collet clamp 16 is also free to rotate, relative to bracket 14, and ball collect 18 is free to swivel and rotate within insert 32. In this way, the various parts of rail system 10 can move about, relative to rail 12, to be able to attach to pins 20, while fastener 44 is loose. When the various parts of system 10 are in desired locations relative to pins 20, each fastener 44 may then be tightened, which simultaneously (1) fixedly attaches bracket 14 to rail 12, (2) fixedly attaches collect clamp 16 to its respective bracket 14, and (3) compresses collet clamp 16, insert 32 and ball collet 18, to fixedly hold onto pin 20. Thus, unlike any currently available or prior art external bone fixation system, adjustability and tightening of each set of components of external bone fixation rail system 10 is fully controlled by only one fastener. By this mechanism, rail system 10 is configured to connect rail 12 to multiple bone pins 20 connected to one or more bones, often at different angles and orientations, for fixation and stabilization.

Rail 12 may be any size or shape, and rails 12 of many differing sizes and/or shapes may be included as part of rail system 10 or in multiple different embodiments of system 10. Rail 12 may, for example, have a cross-sectional shape that is circular, oblong, square, rectangular, or other shape, in various alternative embodiments. In the illustrated embodiment, rail 12 has a circular cross-section and a size designed for fixation of small bones, such as those of the foot or hand. For example, in embodiments of rail system 10 used for fixation of foot and ankle bones, rail 12 may be provided in a relatively short length of between about 2.25 inches and about 2.75 inches or a slightly longer length of between about 3.75 inches and about 4.75 inches. Rail 12 is relatively rigid and may be made of any suitable rigid material, such as but not limited to stainless steel, carbon fiber, other rigid metals, high density plastic and other rigid polymers. When high density plastic is used, for example, rail may be radiolucent. Optionally, in some embodiments, rails 12 may have one or more recesses 22, detents 24 or combinations thereof, which limit the axial sliding capability of brackets 14 mounted to rail 12.

Figure 2A:
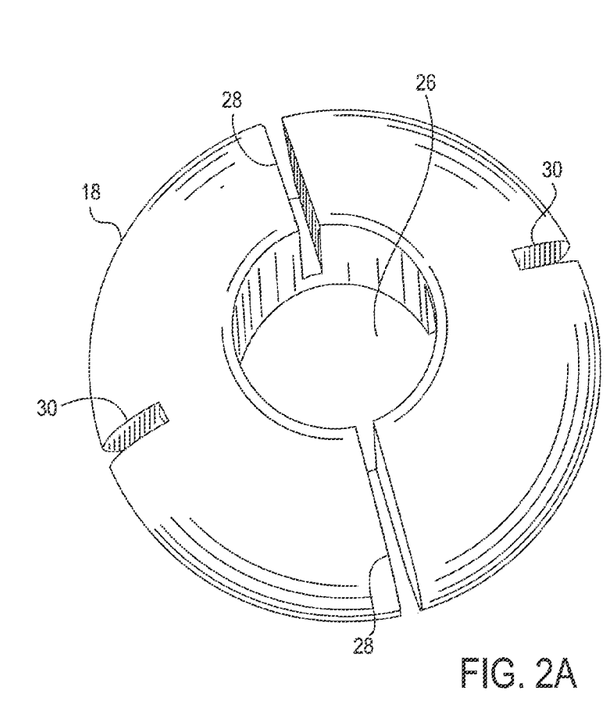
FIGS. 2A and 2B are top perspective and side views, respectively, of a ball of a ball collet assembly, which is part of the external bone fixation rail system of FIG. 1, according to one embodiment.
Figure 2B:
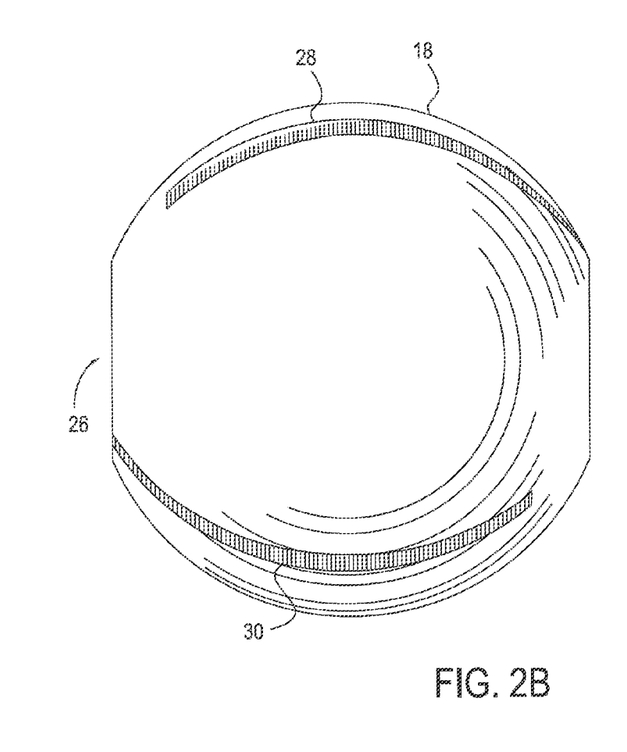

Referring now to FIGS. 2A and 2B, ball collet 18 is illustrated in greater detail. Ball collet 18 may be made of aluminum or a similar crushable material, and it includes an aperture 26 for receiving bone pin 20. In various embodiments, aperture 26 may have any suitable diameter (e.g., 3 mm, 4 mm, 5 mm or 6 mm), to mate with a corresponding diameter pin 20. Ball collet 18 further preferably includes a first pair of slits 28 (or "cuts") and a second pair of slits 30. As can be seen from the side view of ball collet 18, in FIG. 2B, each pair of slits 28, 30 extends approximately 90 percent along the length of ball collet 18, with each pair of perforations 28, 30 extending from opposite sides of ball collet 18. In other words, at one of aperture 26, only the first pair of slits 28 will extend from the aperture through to the periphery of ball collet 18, while at the other end of aperture 26, only the second pair of slits 30 will so extend. The fact that neither pair of slits 28, 30 extends along the entire length of ball collet 18 may help ball collet 18 maintain its structural integrity when compressed by collet clamp 16. At the same time, however, slits 28, 30 provide a "crush zone," such that the application of a compressive force (as provided and explained below) provides a friction fit between ball collet 18 and pin 20. In alternative embodiments, ball collet 18 may be made of different materials, have a different shape and/or have a different number and/or pattern of slits than in the embodiment of FIGS. 2A and 2B. At least one alternative embodiment is described further below.

Figures 3, 4:
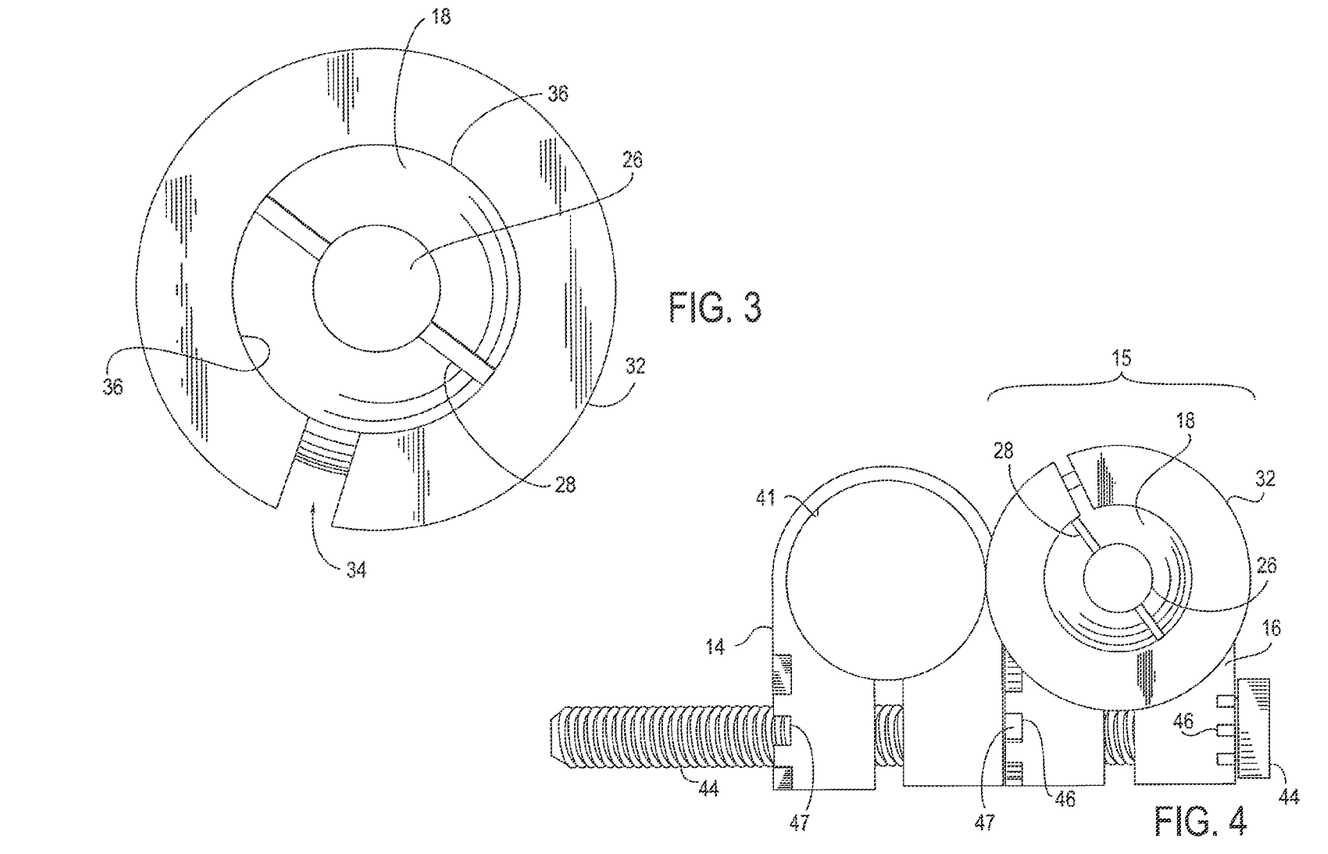
FIG. 3 is an end-on view of a ball and an insert/sleeve of a ball collet assembly, which is part of the external bone fixation rail system of FIG. 1, according to one embodiment.
FIG. 4 is an end-on view of a bracket and ball collet assembly engaged with a single fastener, which is part of the external bone fixation rail system of FIG. 1, according to one embodiment.

Referring now to FIG. 3, ball collet 18 may be supported by an insert 32 (or "sleeve"), in some embodiments. In alternative embodiments, the function of insert 32 may be provided, instead, by a recess or groove integrally built into collet clamp 16. One advantage of insert 32 is that the structure of collet clamp 16 and bracket 14 may be essentially identical, thus allowing a modular, simpler manufacture and assembly of those two parts. Insert 32 may be made of any suitable plastic or similar material, such as polyether ether ketone (PEEK) plastic in one embodiment. In the depicted embodiment, insert 32 is a PEEK plastic sleeve that includes a slit 34 and ridges 36. Slit 34 allows for easier placement of ball collet 18 within insert 32 during assembly, and ridges 36 help retain ball collet 18 within insert 32 once it is inserted. Ball collet 18 is still free to rotate within insert 32 after placement and before collet clamp 16 is tightened by fastener 44. The ability of ball collet 18 to freely rotate within insert 32 allows the surgeon or other user to easily adjust an angle of aperture 26 of ball collet 18 to fit over pin 20 at any of a variety of different angles.

Referring now to FIG. 4, ball collet assembly 15, bracket 14 and fastener 44 are illustrated in greater detail and coupled together. Ball collet 18 resides within insert 32, and insert 32 resides within collet clamp 16. Collet clamp 16 and bracket 14 are coupled together via fastener 44 and may also be mated together via complementary collet clamp surface features 46 and bracket surface features 47. Bracket 14 includes a main aperture 41, through which rail 12 slidably extends when bracket 14 is attached to rail 12. Fastener 44 is a screw, in this embodiment, but may be any of a number of different suitable fasteners in alternative embodiments.

Figure 5A:
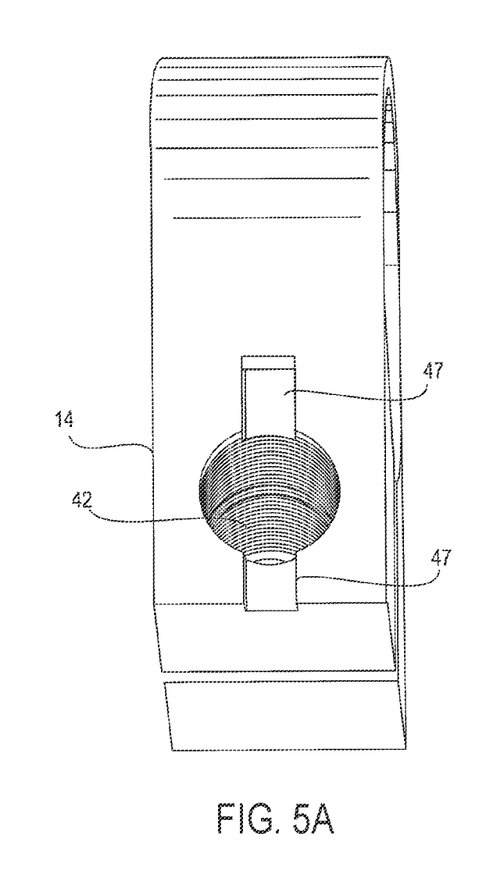
FIGS. 5A and 5B are side perspective views of a bracket and a collet clamp with insert, respectively, which are part of the external bone fixation rail system of FIG. 1, according to one embodiment.
Figure 5B:
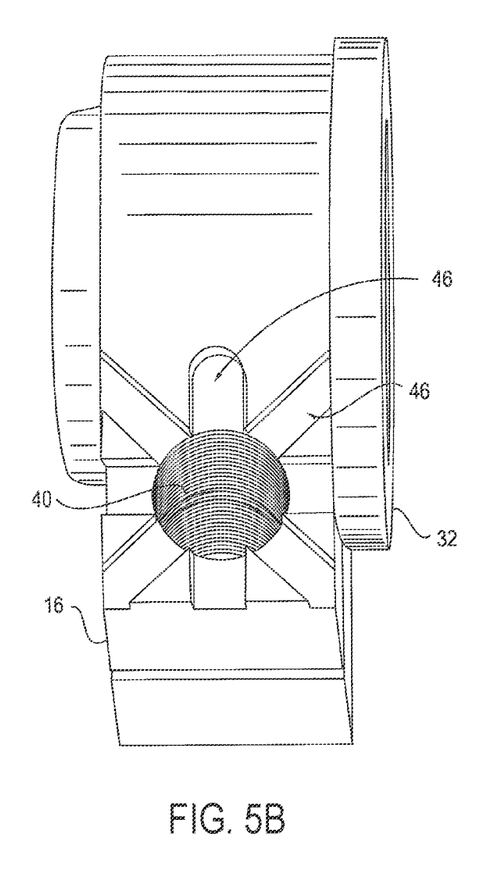

Referring now to FIGS. 5A and 5B, side perspective views of bracket 14 (FIG. 5A) and collet clamp 16 (FIG. 5B) are provided. Collet clamp 16 includes a collet clamp support aperture 40, extending through the flat bottom of that component, and bracket 14 includes a bracket support aperture 42. As mentioned above, in one embodiment bracket 14 and collet clamp 16 may have the same structure and thus be interchangeable. For example, if the image of bracket 14 in FIG. 5A were flipped to show the opposite side of bracket 14, it would look the same as collet clamp 16 in FIG. 5B. In alternative embodiments, bracket 14 and collet clamp 16 may have different structures. Also as mentioned above, bracket 14 and collet clamp 16 may include complementary surface features (bracket surface features 47 and collet clamp surface features 46) on their sides, which mate with one another to provide a more firm and immovable connection between bracket 14 and collet clamp 16 when fastener 44 is tightened. When fastener 44 is loose, collet clamp 16 may be rotated relative to the bracket 14 around an axis defined by collet clamp support aperture 40 and bracket support aperture 42.

In one embodiment, bracket support aperture 42 is threaded, and collet clamp support aperture 40 is not, to make threading fastener 44 through collet clamp 16 and bracket 14 easier. In alternative embodiments, bracket support aperture 42 and collet clamp support aperture 40 are threaded, to provide truly identical structures for modular manufacture and assembly. Given the U-shaped structures of bracket 14 and collet clamp 16, tightening fastener 44 squeezes and provides a friction fit for bracket 14 around rail 12, and prevents further movement of bracket 14 along the length of rail 12. Tightening fastener 44 also squeezes bracket 14 and collet clamp 16 together, thus preventing further rotation of the two components relative to one another. Additionally, tightening fastener 44 squeezes the U-shaped bracket clamp 16, which squeezes insert 32 and ball collet 18, thus crimping/collapsing slits 28, 30, which prevents further rotation of ball collet 18 in insert 32 and firmly affixes ball collet 18 to pin 20. Therefore, tightening of only one, single fastener 44 secures each set of bracket 14 and ball collet assembly 15 relative to one another, to rail 12 and to pin 20. In other words, tightening one fastener 44 sets all of the different axes of rotation for one group of components on external fixation rail system 10. This configuration is highly advantageous, in that it makes tightening, loosening, repositioning and retightening each group of components very simple.

Referring now to FIGS. 6A-6D, another embodiment of an external bone fixation system 100 is illustrated. This embodiment of system 100 may be used for attaching to, and supporting, multiple bone pins in one or more fractured bones. Typically, system 100 is used for fractures of long bones in the lower limb, such as the femur, tibia and fibula. However, system 100 may also be used for long bones in the upper limb, and in some embodiments system 100 may be used for fixation of long bones and smaller bones in the same limb, such as a long bone in the lower leg and one or more ankle and/or foot bones, in one example. Unlike rail system 10 described above, external bone fixation system 100 is generally configured to encircle a limb and thus provide surfaces for attaching to bone pins at locations around the circumference of the limb. (Similar circumferential pin attachment may also be achieved using multiple rail systems 10 disposed around a circumference of an ankle or foot, for example.)

In the illustrated embodiment, external bone fixation system 100 includes a first semi-circular external fixation member 102, a second semi-circular external fixation member 104, four ball collet clamp assemblies 106 attached to second external fixation member 104, and four shafts 108. Each shaft 108 has a first end attached to first external fixation member 102 via a shaft fastener 110 and a second end that has a stop member 114 attached to it. Each shaft 108 passes slidably through an opening in a ball 107 of one of the four ball collet assemblies 106 attached to second external fixation member 104, and the stops 114 prevent the second ends of shafts 108 from passing through the balls 107. Each shaft 108 also includes a hinge 112, located closer to its first end than to its second end.

First and second external fixation members 102, 104 include multiple attachment apertures 103, which may be used for attaching shaft fasteners 110, pin attachment devices (not illustrated) and/or ball collet assemblies 106. Attachment apertures 103 also make first and second external fixation members 102, 104 lighter than they would be without apertures 103. In various embodiments, each of first and second external fixation members 102, 104 may include any suitable number of attachment apertures 103, such as but not limited to between four and forty attachment apertures 103, or more preferably between about twenty and thirty-five attachment apertures 103, and in one embodiment thirty-two attachment apertures 103. In the depicted embodiment, first and second external fixation members 102, 104 both extend approximately 270 degrees around a circle. When assembled within external bone fixation system first and second external fixation members 102, 104 may be aligned such that their open portions face in opposite directions, as seen in FIGS. 6A-6D. Thus, together, first and second external fixation members 102, 104 may form a complete circle around a limb.

First and second external fixation members 102, 104 may have any suitable size, and in various embodiments they may be provided in a variety of different sizes. In one embodiment, for example, first and second external fixation members 102, 104 may be sized such that a diameter measured across the circle that they form together is approximately six and five-eighths inches. Alternative embodiments may range from as small as four inches in diameter or less to as many as ten inches in diameter or more. As an optional feature, first external fixation member 102 may include four lateral protrusions 105 or projections, each of which includes one attachment aperture 103, to which one of shaft fasteners 110 is attached. In other embodiments, both first and second external fixation members 102, 104 may include such lateral protrusions 105, or alternatively neither of them may include lateral protrusions 105. First and second external fixation members 102, 104 may be made out of any suitable metal or polymer, as long as it is sufficiently strong and rigid to provide stable attachment and support of bone pins. In some embodiments, the outer surface of first and second external fixation members 102, 104 may be rough, from a coating on, or a treatment of, the external surface. The rough outer surface may help facilitate attachment of bone pin attachment devices to first and second external fixation members 102, 104.

Figure 6A:
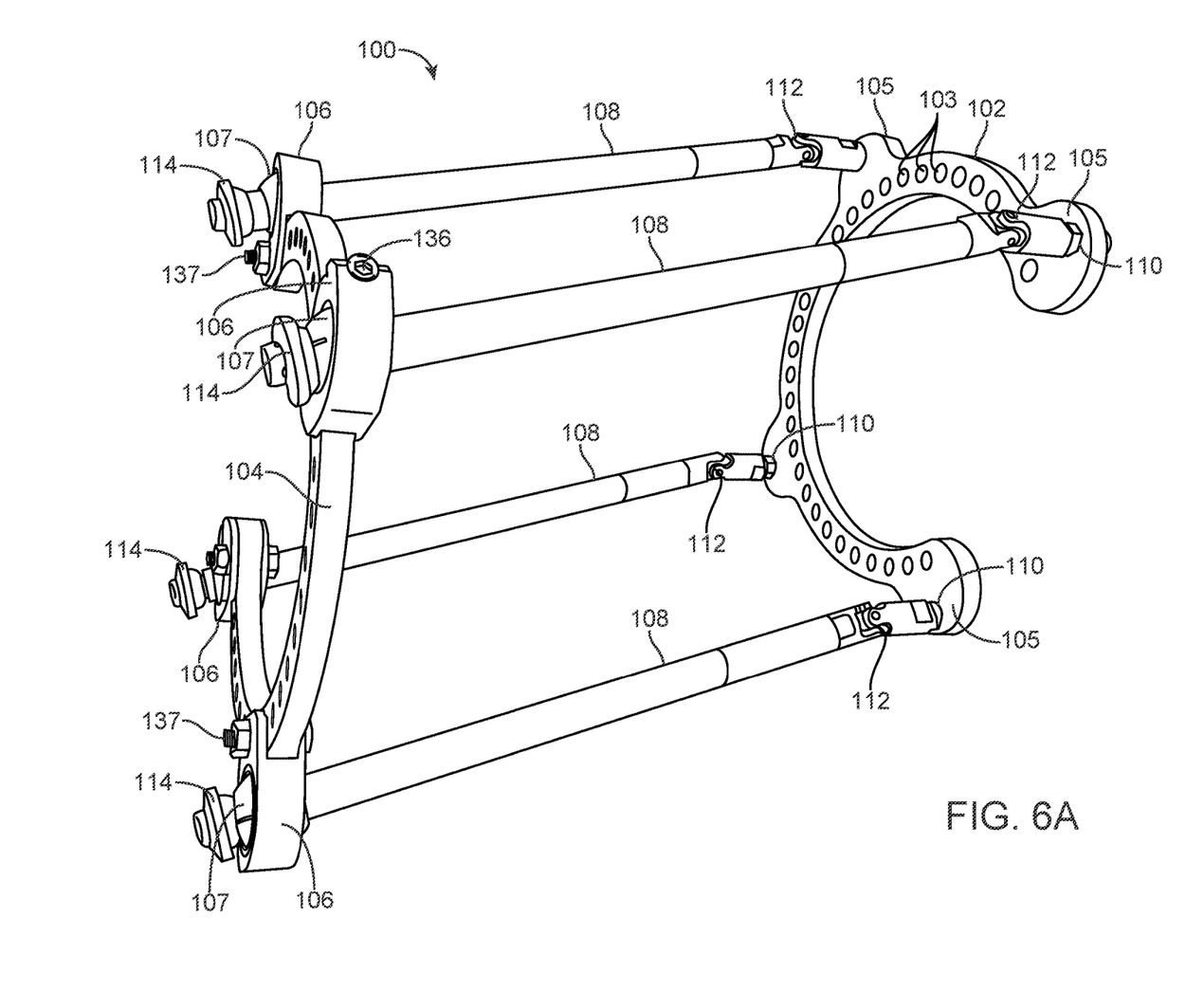
FIGS. 6A-6D are perspective views of another embodiment of an external bone fixation system, in which external fixation members partially encircle a patient's limb, according to one embodiment.
Figure 6B:
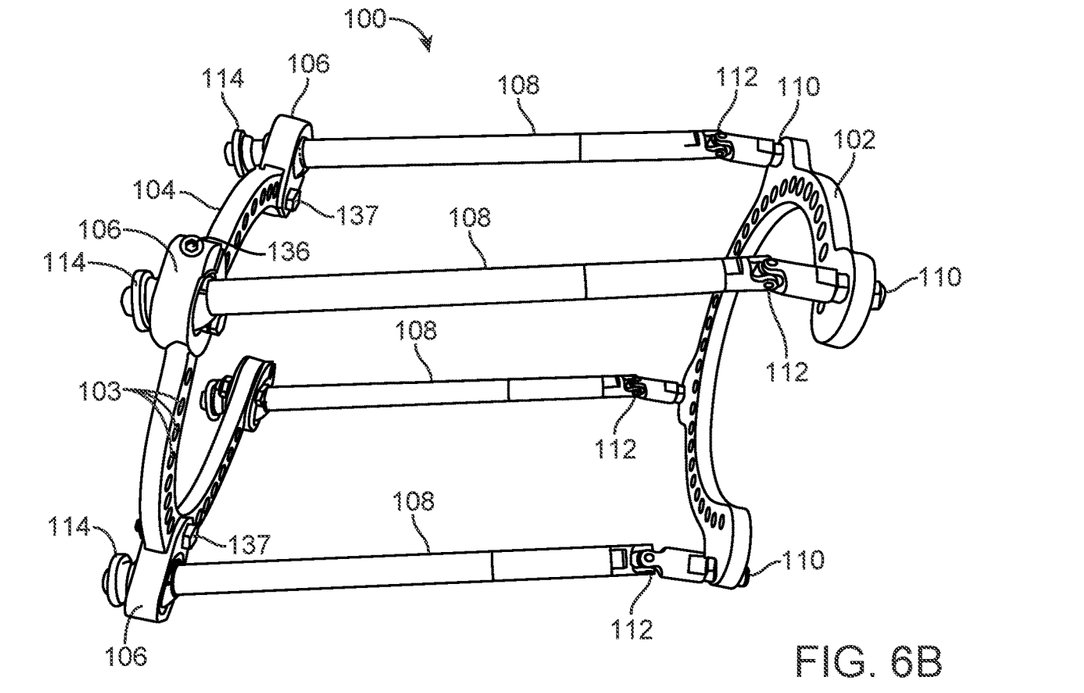
Figure 6C:
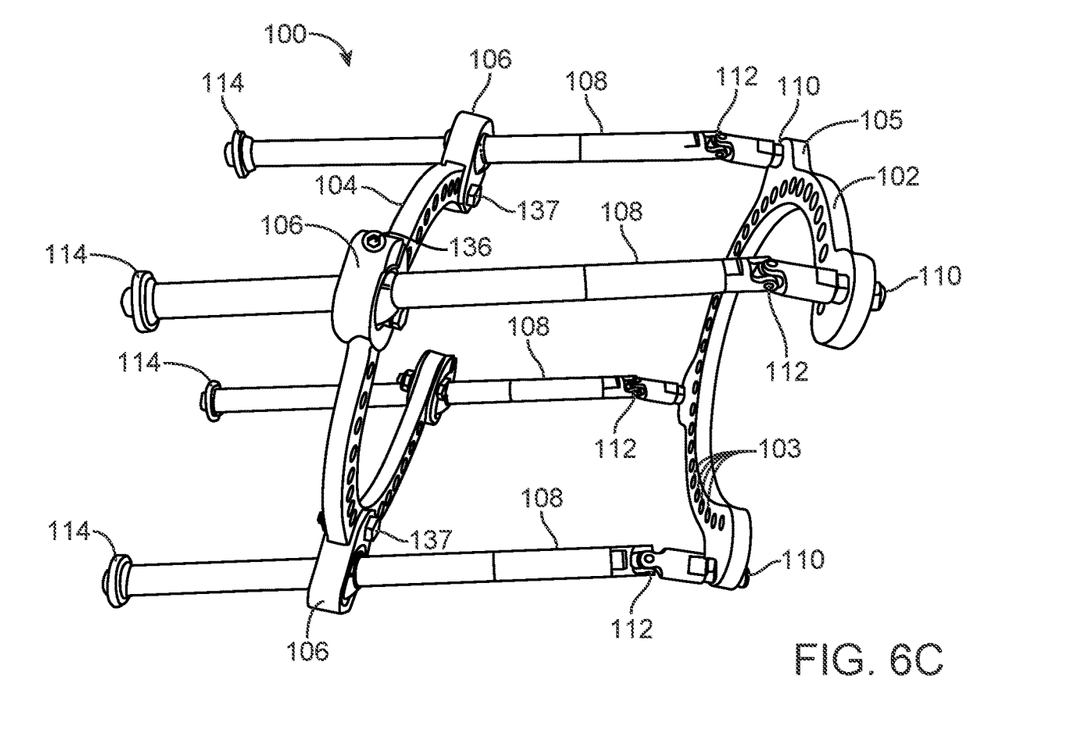
Figure 6D:
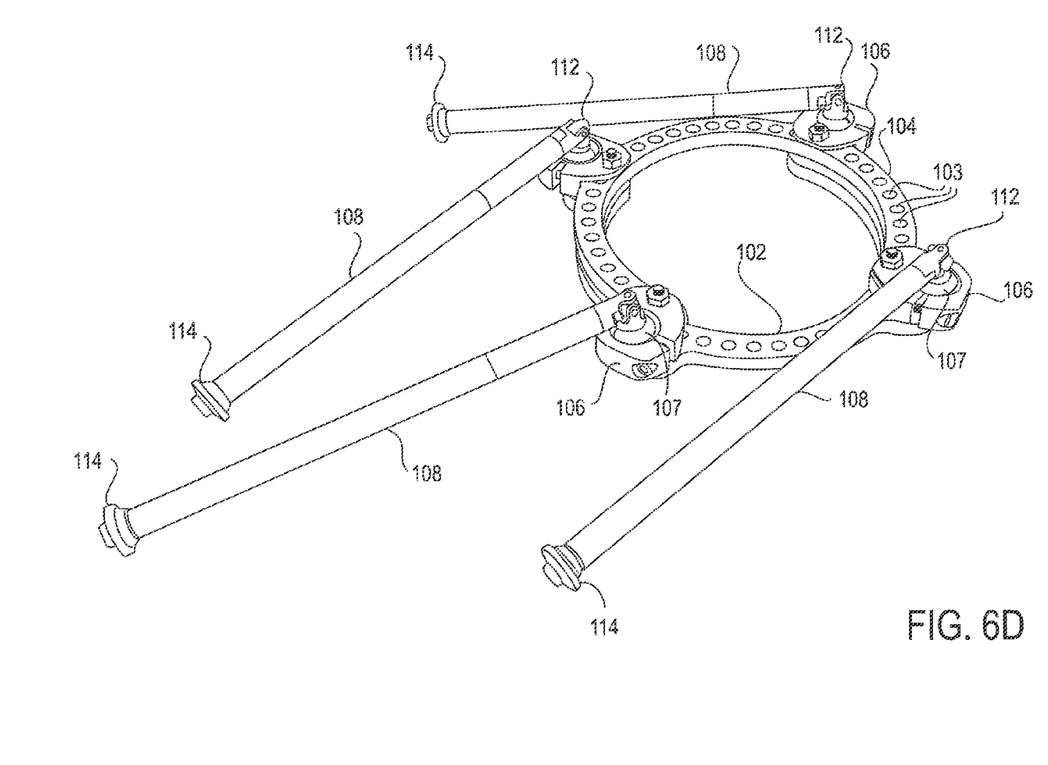

Shaft fasteners 110 may include two bolts and a dowel, with the dowel running through one of attachment apertures 103. In some embodiments, shaft fasteners 110 are free to spin or rotate within their attachment apertures 103, thus allowing shafts 108 to spin, relative to first external fixation member 102. As mentioned above, each shaft 108 also includes hinge 112. Together, the spinning of shaft fasteners 110 and the bending of hinges 112 allows system 100 as a whole to twist. Hinges 112 also allow system 100 to fully collapse from an extended or expanded configuration, as illustrated in FIGS. 6A and 6B, to a fully collapsed configuration, as illustrated in FIG. 6D. In the fully extended configuration, second external fixation member 104 contacts stops 114. In the fully collapsed configuration, second external fixation member 104 is located between hinges 112 and first external fixation member 102, thus allowing hinges 112 to be fully bent. This fully collapsed configuration may be highly advantageous for packaging, transport and storage of system 100. Just as first and second external fixation members 102, 104 may be made of any suitable metal or polymer, so too may shafts 108, hinges 112, shaft fasteners 110 and stops 114 be made of any suitable metal, polymer or combination thereof. In one embodiment, for example, all components of system 100 may be made of metal. In other embodiments, most of the components may be metal, with one or more other components being made of a polymer, such as stops 114 and/or one or more parts of ball collet assemblies 106. In one embodiment, stops 114 are circumferential of rubber parts that are attached to the second ends of shafts 108 and are wider than the outer circumference of the shafts 108. Alternatively, however, stops 114 may be formed as an integral part of shafts 108 (in other words, each shaft 108 and stop 114 is one piece), and shafts 114 may be made of the same material as shafts 108.

Shafts 108 may have any suitable dimensions and configurations. In one embodiment, for example, one shaft 108 may have a length, not including stop 114 or a hinge portion of shaft 108, of about seven and seven-eighths inches. Including the hinge portion, shaft 108 may have a length of about eight and five-eighths inches. The same embodiment of shaft 108 may have a diameter of about one half inch. Each shaft 108 may be a single piece or multiple pieces, in various embodiments. For example, in one embodiment, each shaft 108 may include a separate hinge portion, which may be attached to the first end of shaft 108. In alternative embodiments, each shaft 108 may include an integral hinge portion. Shafts 108 may be made of stainless steel, aluminum, titanium, or any other suitable metal or polymer.

In use, external bone fixation system 100 may first be extended from its collapsed configuration (such as in a package) to its fully extended (FIG. 6A) or partially extended (FIG. 6C) configuration. System 100 may then be positioned around a patient's lower limb (or alternatively an upper limb) by positioning first and second external fixation members 102, 104 around the limb. Alternatively, first and second external fixation members 102, 104 may be passed over the limb with system 100 in the collapsed configuration, and then system 100 may be expanded. The positions of first and second external fixation members 102, 104 may be adjusted, according to the desire of the physician, to allow the best positioning relative to any bone pins to be attached to system 100. When a desired positioning is achieved, ball collet assemblies 106 may be tightened, to lock second external fixation member 104 rigidly and immovably to shafts 108. At this point, system 100 may be attached to any number of bone pins extending out of the patient's bone(s), using any number of bone pin attachment devices, which are not illustrated here. These bone pin attachment devices may be any currently available or future bone pin attachment devices, and they may be provided as part of system 100 or provided separately, in various embodiments. The bone pin attachment devices attach, in some embodiments, to attachment apertures of first and second external fixation members 102, 104. The adjustability of system 100 provided by ball collet assemblies 106, hinges 112 and spinning shaft fasteners 110 is believed to be highly advantageous to users and a significant improvement over currently available external bone fixation systems.

Figure 7:
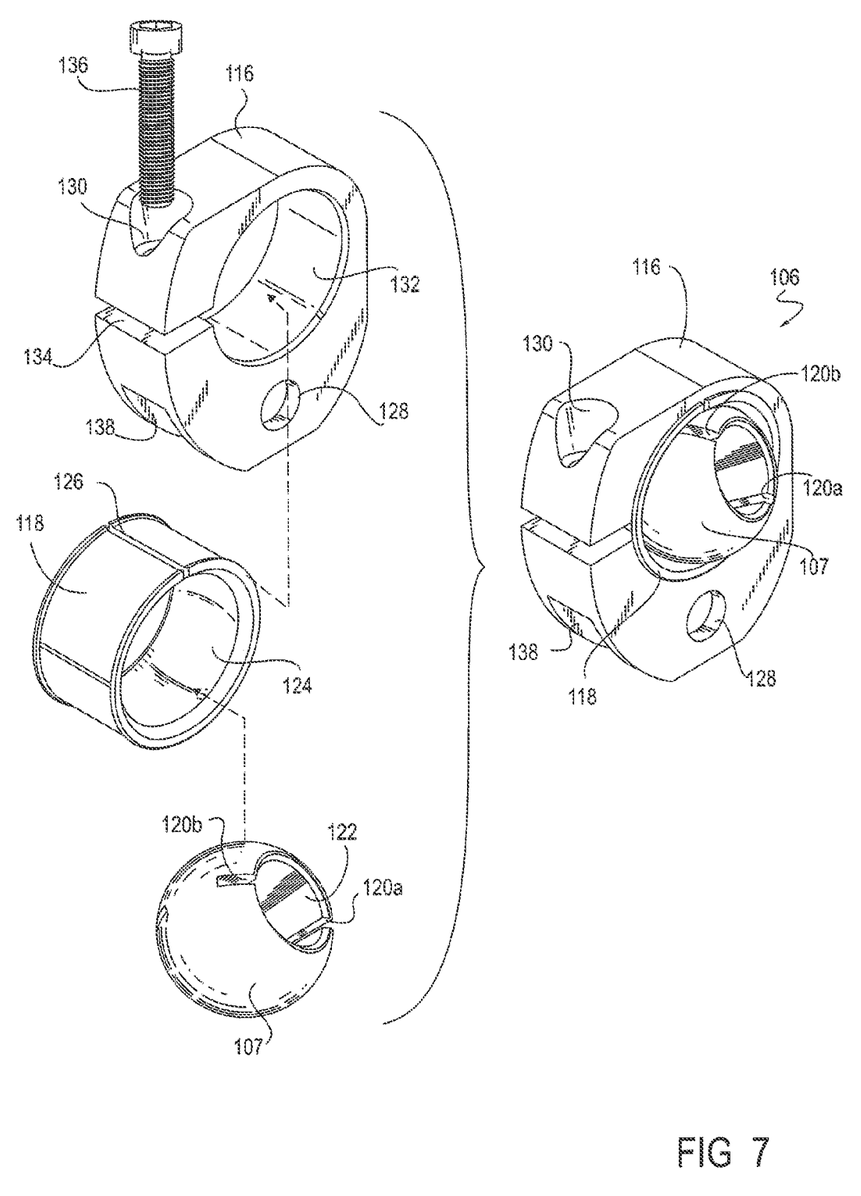
FIG. 7 is a perspective view, with a portion of the figure exploded, of a ball collet assembly, which is part of the external bone fixation rail system of FIGS. 6A-6D, according to one embodiment.

With reference now to FIG. 7, ball collet assembly 106 of external bone fixation system 100 is illustrated in greater detail. In this embodiment, ball collet assembly 106 includes a metallic ball 107, fitted inside an insert 118, which in turn is fitted inside a collet clamp 116. Ball 107 includes two slits 120a, 120b and a central ball opening 122. In this embodiment, a first slit 120a is cut all the way through the full thickness of ball 107 (from central ball opening 122 to the ball's outer surface), along its entire length, and a second slit 120b extends through the full thickness of ball 107 only on the two ends of second slit 120b. A middle portion of second slit 120b is only on the inside surface of ball 107 (starting from central ball opening 122 but not extending to the ball's outer surface). When compressing pressure is exerted on ball 107, via collet clamp 116 and insert 118, slits 120a, 120b allow ball 107 to partially collapse, and thus tightly hold onto one of shafts 108, while still maintaining its general spherical shape and structural integrity. In some embodiments, ball 107 may be made of aluminum and may have a rough textured outer surface, which may enhance the ability of ball 107 to adhere to the inner surface of insert 118. Ball 107 may have any suitable size, such as about thirteen-sixteenths of an inch in one embodiment, or between half an inch and one inch in various alternative embodiments.

Insert 118 may be made of a polymeric material, such as PEEK plastic in one embodiment, and may include a central insert opening 124 and one or more slits 126. In alternative embodiments, insert 118 may be made of a different material, such as metal, or may be eliminated from ball collet assembly 106 completely. In embodiments without insert 118, collet clamp 116 may include an inner surface, forming an inner clamp opening 132, which has one or more features (such as outer rims, texture, etc.) to replicate insert 118. In the embodiment illustrated, however, insert 118 fits within inner clamp opening 132 and is configured to partially collapse around ball 107 when compressive force is exerted upon it by collet clamp 116. Insert 118 may include outer rims on the edges of its inner surface, in order to better hold onto ball 107.

Collet clamp 116 may be made of aluminum, another metal, PEEK plastic, or another polymeric material. Collet clamp 116 may extend around most of a complete circumference of inner clamp opening 132, but may include a slit 134 to allow inner clamp opening 132 to shrink when collet clamp 116 is tightened. Collet clamp 116 typically includes at least one attachment aperture 128, for passage of an attachment fastener 137 (not shown in FIG. 7, see FIGS. 6A-6D), for attaching clamp 116 to second external fixation member 104, and a cutout portion 138 for allowing collet clamp 116 to fit over second external fixation member 104. Attachment fastener 137 may be a bolt and a nut, for example, or alternatively any other suitable fastening device. Collet clamp 116 also typically includes a tightening aperture 130, for passage of a tightening fastener 136 for tightening clamp. Tightening fastener 136 may be a bolt, a screw or the like, in one embodiment, and tightening aperture 130 may include threads on part or all of its surface, for mating with tightening fastener 136 and allowing collet clamp 116 to be tightened. In some embodiments, Helicoil may be added to the threaded portion of tightening aperture 130, to add strength to the connection between tightening fastener 136 and the threads. Additionally, the threads of tightening fastener 136 may be coated with Teflon for smoother tightening action and to facilitate tightening and loosening tightening fastener 136 multiple times.

Figure 8:
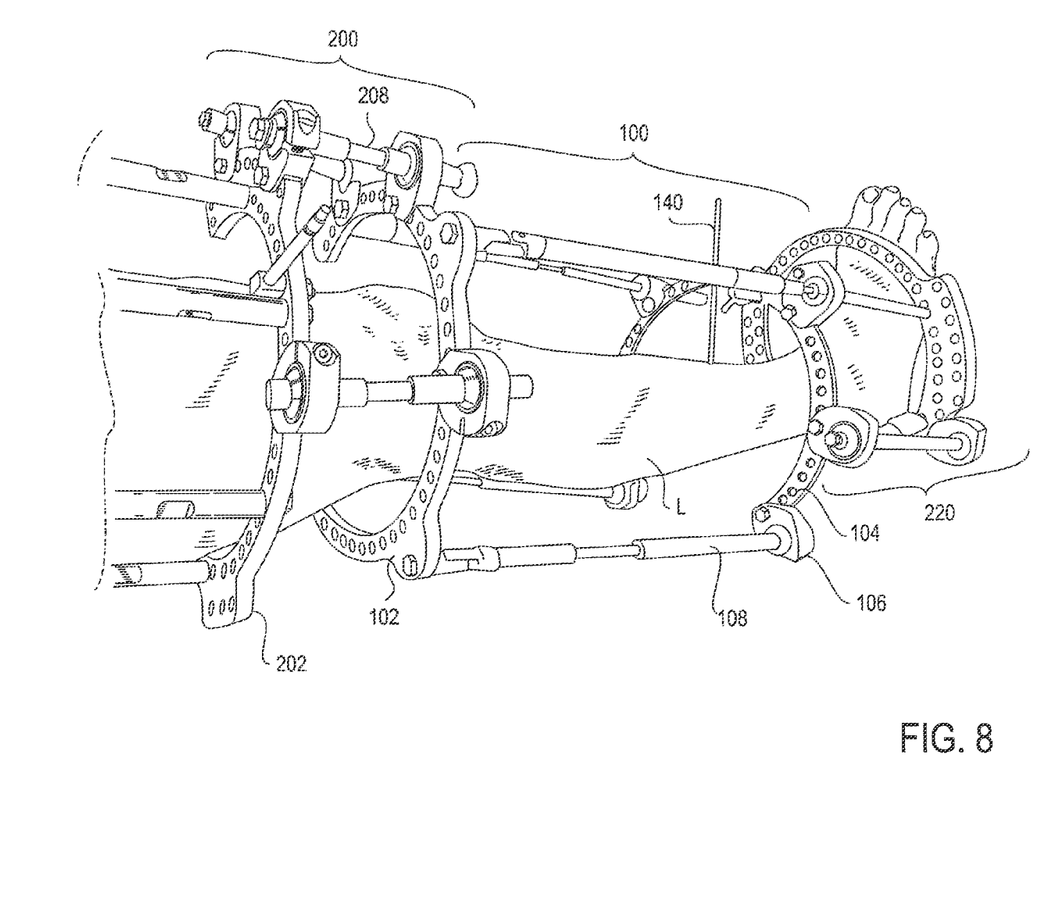
FIG. 8 is a perspective view of a patient's limb, with the external bone fixation system of FIGS. 6A-6D in position and coupled with an additional expansion system, according to one embodiment.

Referring now to FIG. 8, in some embodiments, external bone fixation system 100 may be used with additional systems or with add-on sets of components. For example, as illustrated, a first set of add-on external bone fixation components 200 may be attached to a proximal end of system 100, and a second set of add-on external bone fixation components 220 may be attached to a distal end of system 100. These add-ons allow system 100 to be extended to cover a longer length of a lower limb L (or upper limb in alternative embodiments). Any given set of components, such as first set 200, may include any suitable combination of any of the components described above, as well as any variations on such components (different sizes, configurations, numbers of components, materials, etc.). In the illustrated embodiment, for example, first set 200 includes an additional external fixation member 202, multiple additional shafts 208 and multiple additional ball collet assemblies 206. FIG. 8 also illustrates one bone pin 140, as is typically attachable to one of the external fixation members 102, 104, 202. The embodiment illustrated in FIG. 8 is only one example of how system 100 may be combined with additional sets of components, 200, 220. In alternative embodiments, any suitable number, combination and configuration of additional components may be combined with system 100 for use on a given patient.

Figure 9:
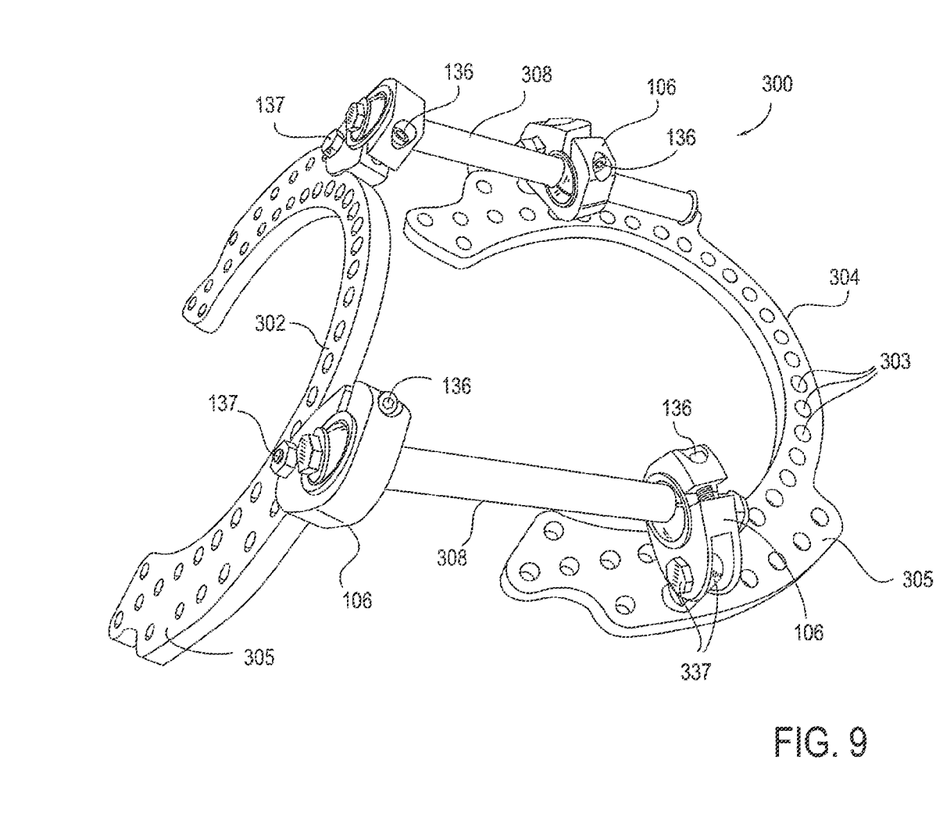
FIG. 9 is a perspective view of another embodiment of an external bone fixation system, which may in some embodiments be added to another fixation system, such as the system of FIGS. 6A-6D.

With reference to FIG. 9, another embodiment of an external bone fixation system 300 (or a set of add-on components for system 100) is illustrated. In this embodiment, system 300 includes a first external fixation member 302 and a second external fixation member 304, both of which are structurally the same and include lateral protrusions 305 and multiple attachment apertures 303. Four ball collet assemblies 106 are attached at four different locations on attachment apertures 303 on lateral protrusions 305. Ball collet assemblies 106 may be the same, similar or differently structured, as compared to previously described embodiments. Shafts 308 connect the first and second external fixation members 302, 304 together, via ball collet assemblies. In this embodiment, shafts 308 are significantly shorter than shafts 108 described previously. Thus, system 300 may be useful for covering a shorter portion of a body, such as a foot/ankle portion or a hand/wrist portion of a body. This embodiment also differs from those previously described in that two of ball collet assemblies 106 are attached to second external fixation member 304 via a post fastener 337. In some embodiments, post fastener 337 may be free to rotate within its attachment aperture 303, while in alternative embodiments it may rigidly fix ball collet assembly to second external fixation member 304. In either case, post fastener 337 allows first and second external fixation members 302, 304 to be aligned at right angles or other angles, relative to one another. This may be especially useful for attaching system 300 to bones in and around an ankle, for example. Again, external bone fixation system 300 is merely one example of a combination of components described herein for external bone fixation.

The above description is not intended to limit the scope of the following claims. Rather, modifications in structure, function or result are intended to be covered by the claims. Various changes, additions, omissions, and modifications can be made to the illustrated embodiments, without departing from the spirit of the present invention. All such modifications and changes are intended to be covered by the following claims.

I claim:

1. A method for attaching an external bone fixation system to one or more bones in a lower limb of a patient, the method comprising:
    positioning a first semi-circular external attachment fixation member over the lower limb at a first location;
    attaching four ball collet assemblies to a second semi-circular external fixation member with four attachment fasteners;
    sliding the second semi-circular external fixation member along four shafts, each shaft attached to the first semi-circular external fixation member and extending through a respective central opening of a respective one of the four ball collet assemblies attached to the second semi-circular external fixation member, to thereby position the second semi-circular external fixation member over the lower limb at a second location, each of the four ball collet assemblies being configured to slide along an entire length of a respective one of the four shafts from the first semi-circular external fixation member to respective second ends of each of the four shafts;
    tightening four tightening fasteners to tighten the four ball collet assemblies attached to the second semi-circular external fixation member to fix the four ball collet assemblies immovably to the four shafts, thus locking positions of the first semi-circular external fixation member, the second semi-circular external fixation member and the four shafts, relative to one another; and
    attaching a first bone pin attachment member coupled with the first semi-circular external fixation member with a first bone pin extending out of a first bone in the lower limb.

2. The method of claim 1, further comprising twisting the first semicircular external fixation member, relative to the second semi-circular external fixation member, by bending the four shafts at four hinges in the shafts, wherein each of the four shafts includes one of the four hinges.

3. The method of claim 1, further comprising straightening the four shafts via hinges located on the four shafts, before sliding the second semi-circular external fixation member from a first position, in which it is located between the four hinges and the first semi-circular external fixation member, to a second position, in which the hinges are located between the first and second semi-circular external fixation members.

4. The method of claim 1, wherein sliding the second semi-circular external fixation member along the four shafts comprises expanding the external bone fixation system from a collapsed configuration to an expanded configuration by straightening the four shafts at four hinges.

5. The method of claim 1, wherein sliding the second semi-circular external fixation member along the four shafts comprises sliding the second semi-circular external fixation member until it contacts four stop members attached to ends of the four shafts.

6. The method of claim 1, further comprising attaching a second bone pin attachment member coupled with the first semi-circular external fixation member with a second bone pin extending out of the first bone or a second bone in the lower limb.

7. The method of claim 1, further comprising attaching a second bone pin attachment member coupled with the second semi-circular external fixation member with a second bone pin extending out of the first bone or a second bone in the lower limb.

8. The method of claim 1, wherein tightening each of the four ball collet assemblies over each of the four shafts comprises tightening only one tightening fastener of each of the four ball collet assemblies.

* * * * *